(12) United States Patent
Goodbread et al.

(10) Patent No.: US 8,752,416 B2
(45) Date of Patent: Jun. 17, 2014

(54) RESONANT CONDUCTOR MEASUREMENT SYSTEM AND METHOD

(71) Applicants: Joseph H. Goodbread, Portland, OR (US); Juerg Dual, Zumikon (CH)

(72) Inventors: Joseph H. Goodbread, Portland, OR (US); Juerg Dual, Zumikon (CH)

( * ) Notice: Subject to any disclaimer, the term of this patent is extended or adjusted under 35 U.S.C. 154(b) by 0 days.

(21) Appl. No.: 13/657,617

(22) Filed: Oct. 22, 2012

(65) Prior Publication Data

US 2013/0139573 A1  Jun. 6, 2013

Related U.S. Application Data

(63) Continuation of application No. 12/378,534, filed on Feb. 17, 2009, now Pat. No. 8,291,750.

(51) Int. Cl.
*G01N 11/16* (2006.01)
(52) U.S. Cl.
USPC ........................................... 73/54.41
(58) Field of Classification Search
None
See application file for complete search history.

(56) References Cited

U.S. PATENT DOCUMENTS 5,837,885 A * 11/1998 Goodbread et al. .......... 73/32 A
7,434,457 B2   10/2008 Goodwin et al.
8,291,750 B1 * 10/2012 Goodbread et al. ......... 73/54.41

OTHER PUBLICATIONS

Agoston, Evaluation of a vibrating micromachined cantilever sensor for measuring the viscosity of complex organic liquids, Sciencedirect.com, Elsevier, Sensors and Actuators, 2005, Vienna, Austria.
Goodwin, A Vibrating Edge Supported Plate, Fabricated by the Methods of Micro Electro Mechanical System for the Simultaneous Measurement of Density and Viscosity: Results for Methylbenzene and Octane at Temperatures between (323 and 423) K and Pressures in the Range (0.1 to 68) MPa, Journal of Chemical and Engineering Data, 2006, vol. 51, No. 1, U.S.
Requa, Electromechanically driven and sensed parametric resonance in silicon microcantilevers, Applied Physics Letters, 2006, vol. 88, Issue 26, CA, U.S.

* cited by examiner

*Primary Examiner* — Hezron E Williams
*Assistant Examiner* — Gregory J Redmann
(74) *Attorney, Agent, or Firm* — Timothy E. Siegel Patent Law, PLLC; Timothy E. Siegel

(57) ABSTRACT

A method of measuring properties of a fluid that uses a conductor electrically connected to a current source. A magnetic field is created about the conductor and the conductor is introduced into the fluid medium. A current waveform, having a frequency, is periodically passed through the conductor, so as to cause the conductor to move, due to force exerted on the conductor from interaction of the current and the magnetic field. The conductor movement is sensed, producing a sense signal that is amplified into an amplified sense signal. The phase relationship between the current waveform and the amplified sense signal is measured and the current waveform frequency is adjusted to create a phase lock loop. The frequency when the phase lock loop is in lock state is measured as the phase between the excitation and the measured sense signal is varied, and fluid properties are calculated from the measured frequencies.

13 Claims, 20 Drawing Sheets

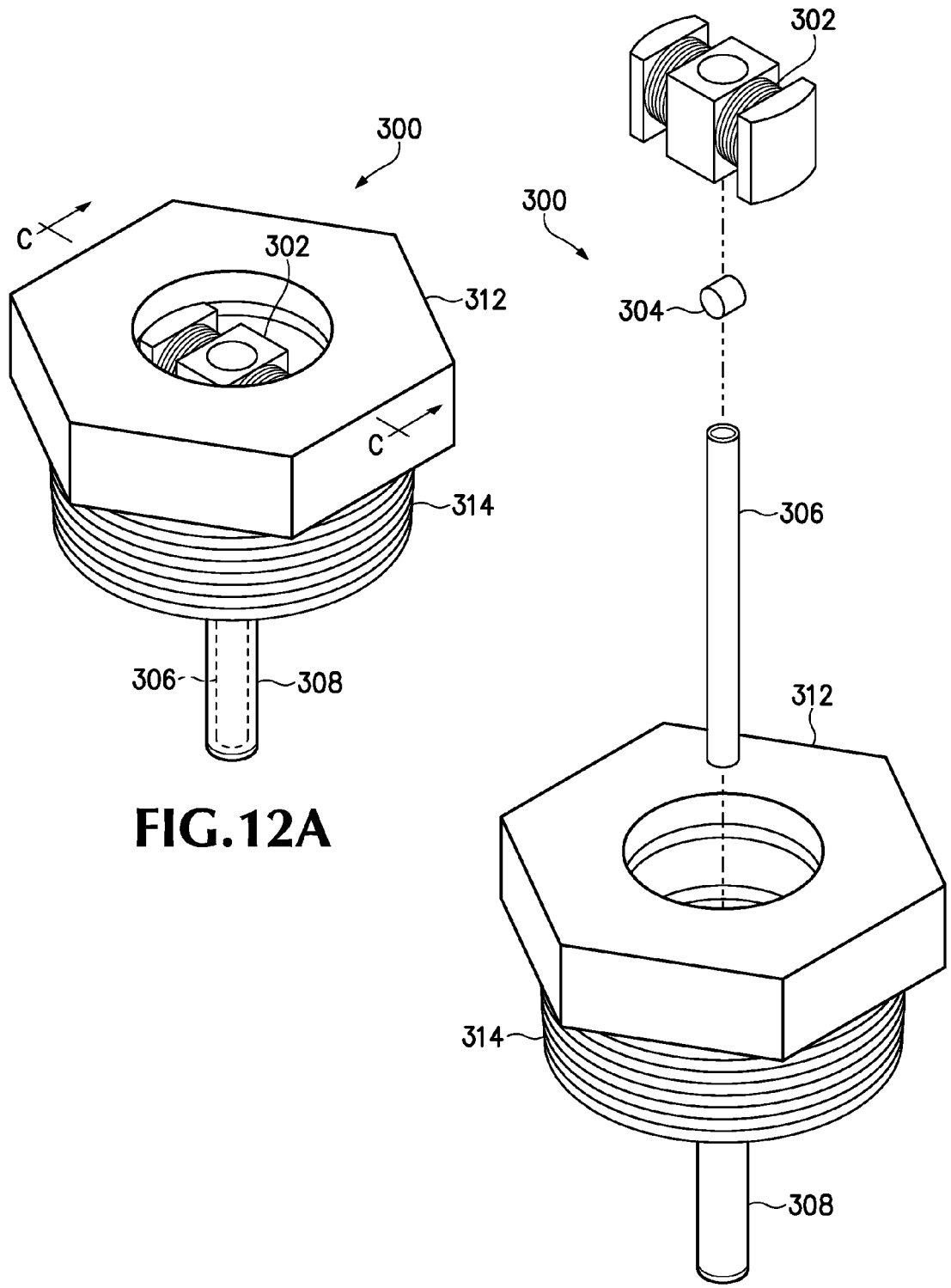

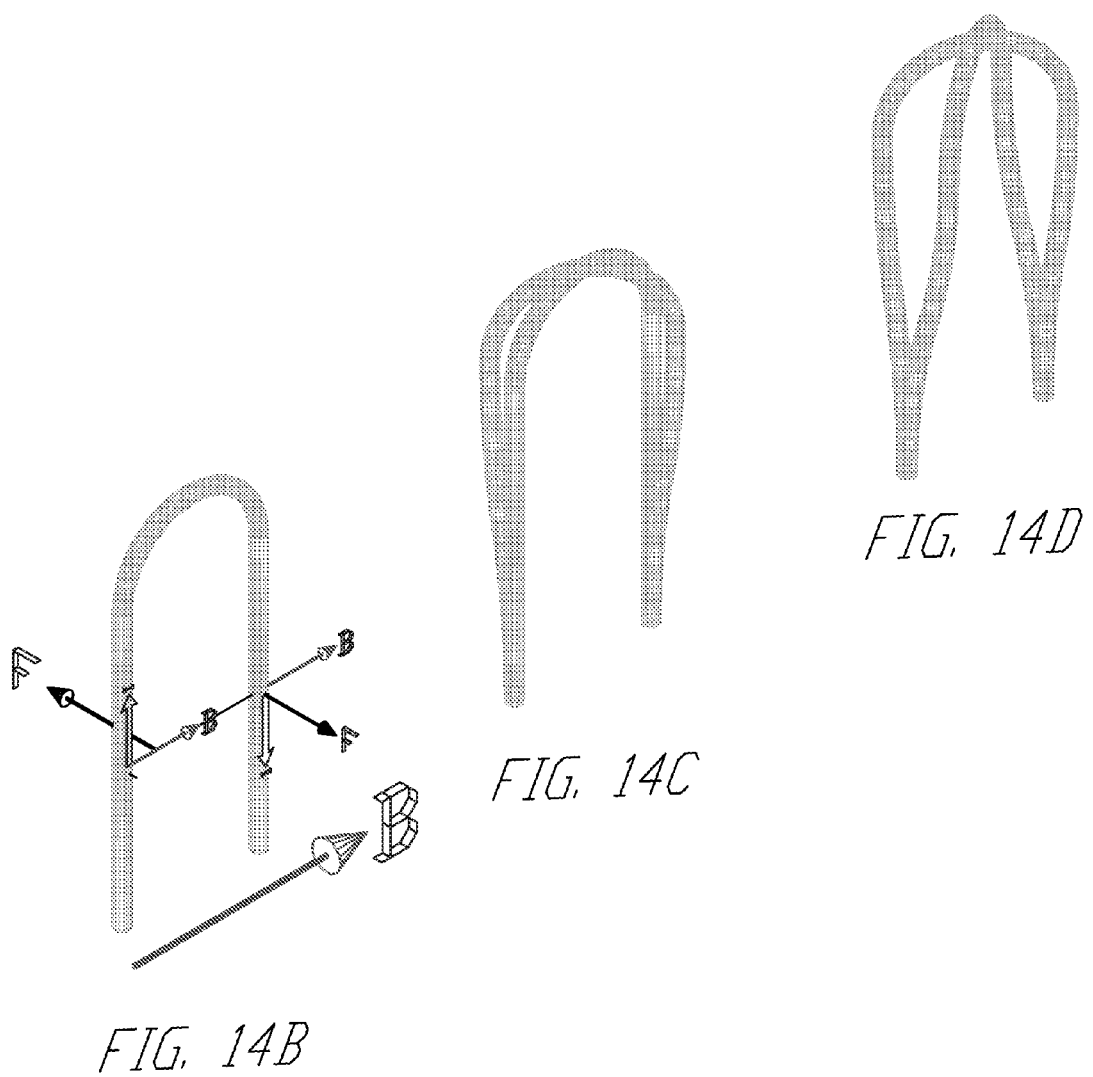

RESONANT CONDUCTOR MEASUREMENT SYSTEM AND METHOD

RELATED APPLICATIONS

This application is a continuation of application Ser. No. 12/378,534 filed Feb. 17, 2009, now U.S. Pat. No. 8,291,750, and which is hereby incorporated by reference as if fully set forth herein.

BACKGROUND

The present invention has to do with a method of measuring induced vibrations, over a sequence of periods, in a damped vibratory system and more particularly to the correction of an erroneous DC signal produced by an amplifier, together with low frequency interference, in such a system. One important application of this technology is the measurement of damping. The present invention also has to do with novel resonator designs, adapted to measure a wide range of fluid characteristics in a wide range of physical media.

Although a wide range of resonators currently exist, there is still a problem with separating out the effects of viscosity from fluid density and elasticity. There is a need for additional resonator designs for working with a wide range of physical media and producing data sufficient to separate the effects of viscosity, fluid density and elasticity.

The measurement of damping, in a damped vibratory or resonant system, finds many application in the industrial arts, among the most important being the measurement of viscosity. One method of measuring viscosity, disclosed in U.S. Pat. No. 5,837,885, involves the perturbation of a fluid by a transducer vibrating near its resonant frequency. The excitation of the transducer is periodically stopped, and after a pause the transducer vibrations are measured. The phase of the received signal is logically "anded" with a phase-shifted signal, which is produced by adding a phase shift $\delta\Phi$ to the excitation signal, producing a control signal which is zero when the two signals are 90° separate in phase. The control signal is used to adjust the excitation frequency in the next iteration. After a number of iterations, typically on the order of 500, with each taking iteration about 1 millisecond, the phase of the received signal should be 90° different from the phase-shifted signal and the frequency should not change from one iteration to the next. The frequency at this state (phase-lock state) is measured. In order that a measurement of damping, and therefore viscosity, can be derived from this frequency, the phase is shifted in sequential periods, each of about one second, by $\delta\Phi$; $-\delta\Phi$ and then $\delta\Phi$ again, with the three resulting frequency values being used to determine damping, as explained further in the Detailed Description. The value of $\delta\Phi$ is typically 22.5° or 45°.

The patent discussed above represents a significant advancement in the art of viscosity measurement, with the method and apparatus disclosed gaining widespread acceptance in the field. Nevertheless, possible implementations of this method are limited to a set of applications, which it would be desirable to broaden, although already quite broad.

One set of problems is caused by a DC offset introduced by the amplifier used to amplify the sensed transducer signal. Every amplifier introduces some DC offset, however slight, into its output signal. This DC offset varies with time and temperature. For many electrical devices there is a tradeoff between accuracy and an added cost for expensive components that introduce less DC offset into the system. It is desirable to have a design that permits the use of less expensive components and yet returns a highly accurate result. The DC offset is a potential source of amplifier saturation with attending system nonlinearity, whereas minimizing the potential error caused by the DC offset adds to system complexity.

Unfortunately, the switching between excitation periods and sensing periods in the method of the '885 patent makes it counterproductive to introduce a simple high pass filter into the system to filter out the erroneous DC voltage introduced by the amplifier. Transients that result from the switching process typically have frequency components of frequencies comparable to that of the vibration mode being measured, and thus are passed or even amplified by a conventional high-pass filter. Further complicating the task of reducing the DC offset is the fact that it is the DC offset specifically during the sense periods that should be corrected. Any method not timed to avoid being affected by the excitation period receive signal would risk corrupting the sense period measurement. Not only would such a method not effectively address the problem, but it could even make it worse.

One problematic condition is the measurement of fluid viscosity in an environment that includes a low frequency vibration. This condition occurs in many environments in which it is desired to measure viscosity, for example an industrial or treatment plant in which fluid is being pumped. The pump typically will introduce low frequency vibrations, which may interfere with the frequency measurement, leading to a less certain reading. There is even a possibility that such low frequency vibrations could defeat the phase-lock process, making it impossible to obtain a reading. Low frequency vibrations caused by a physical shock to the viscometer can have the same effect.

Accordingly, it would be desirable to have a method in which an erroneous DC signal produced by a system amplifier and low frequency vibrations caused by ambient noise or a sudden shock to the system could be reduced in amplitude. The frequent switching between excitation and sensing modes greatly complicates the task of originating such a system.

SUMMARY

In a first separate aspect, the present invention is a method of measuring properties of a fluid that uses a conductor electrically connected to a current source, so as to permit the current source to send a current through the conductor. A magnetic field is created about the conductor and the conductor is introduced into the fluid medium. A current waveform, having a frequency, is periodically passed through the conductor, so as to cause the conductor to move, due to force exerted on the conductor from interaction of the current and the magnetic field. The conductor movement is alternately sensed and a sense signal is produced at a sense signal node and is amplified to produce an amplified sense signal. The phase relationship between the current waveform and the amplified sense signal is measured and the current waveform frequency is adjusted so as to create a phase lock loop. The frequency when the phase lock loop is in lock state is measured as the phase between the excitation and the measured sense signal is varied, and fluid properties are calculated from the measured frequencies.

In a second separate aspect the present invention may take the form of an apparatus for measuring properties of a fluid or compliant solid, such as a gel. The apparatus includes a conductor electrically connected to a current source, so as to permit the current source to send a current through the conductor and a magnet placed to create a magnetic field about the conductor. A controller is connected to the current source and commands the current source to periodically send a current waveform, having a frequency, through the conductor, so as to cause the conductor to move, due to force exerted on the conductor from interaction of the current and the magnetic field. A sensor is adapted to sense the conductor movement and produce a sense signal at a sense signal node and an amplifier is responsive to the sensor to amplify the sense signal to produce an amplified sense signal. Also, a phase detector is adapted to measure phase relationship between the current waveform and the amplified sense signal. The current source controller is responsive to the phase detector and is adapted to cause the current source to adjust the current waveform frequency so as to create a phase lock loop. Also, a frequency detector detects the current waveform frequency when the phase lock loop is in lock state and a logic unit 142 calculates fluid properties from the measured frequency.

Other features of the present invention will be apparent from the accompanying drawings and from the detailed description that follows.

BRIEF DESCRIPTION OF THE DRAWINGS

Exemplary embodiments are illustrated in the drawings. It is intended that the embodiments and figures disclosed herein are to be considered illustrative rather than restrictive.

FIG. 12A is a perspective cut-away view of a preferred embodiment of a transducer configuration.

FIG. 12B is an exploded view of the transducer configuration of FIG. 12A.

FIG. 14B is an additional illustration of the transducer configuration of FIG. 14A, showing the direction of magnetic flux.

FIG. 14C is another additional illustration of the transducer configuration of FIG. 14A, showing torsion of the wire loop.

FIG. 14D is still another additional illustration of the transducer configuration of FIG. 14A, showing maximum torsion of the wire loop.

DETAILED DESCRIPTION OF THE PREFERRED EMBODIMENT

Figure 1:
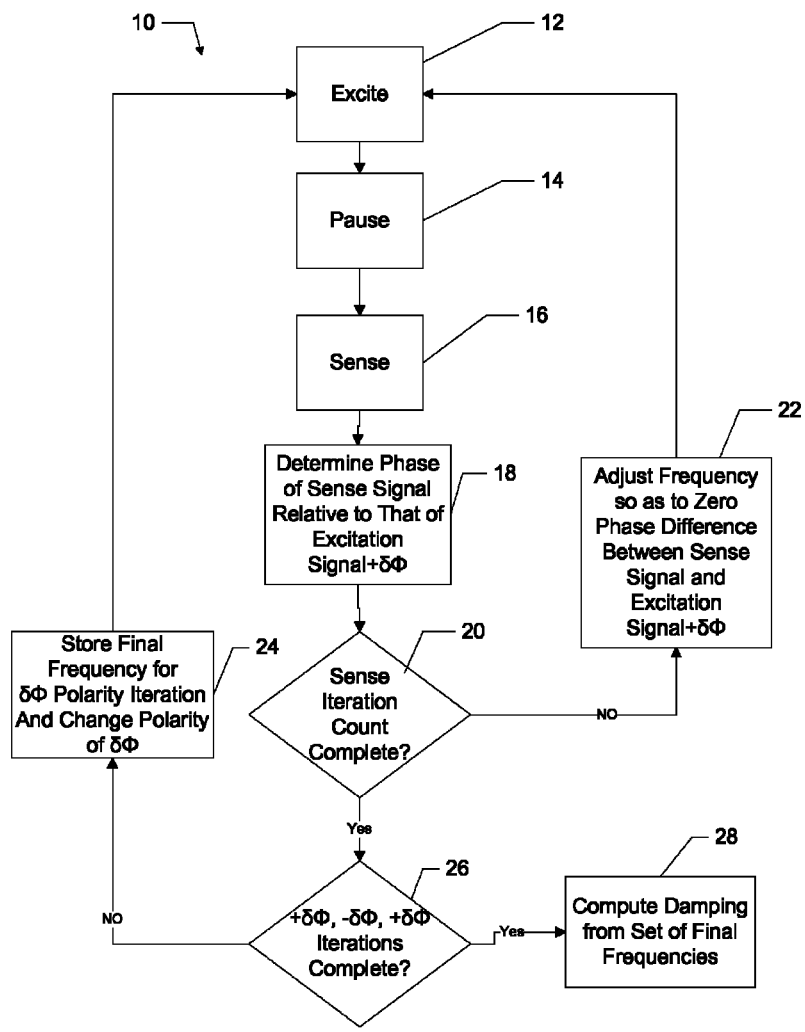
FIG. 1 is a flow diagram of a method of determining damping in a damped vibratory system, which forms the environment of the present invention.

The present invention may be instituted in the environment of a damped-vibratory-system damping-measurement process 10 shown in flowchart form in FIG. 1. A transducer is used to periodically excite a resonator immersed in a fluid medium (block 12), by vibrating the resonator at an excitation frequency. Alternately, after a pause (block 14), the movement of the resonator is sensed by the transducer (block 16). After this, the phase of the sensed signal relative to the excitation signal phase, plus a phase shift $90°+\delta\Phi$, is computed (block 18). In one preferred embodiment this process is repeated for a fixed number of iterations, typically on the order of 500. In this embodiment, the next step is to determine if the fixed number of iterations has been reached (decision box 20). If the iteration count is not complete, the frequency is adjusted (block 22) in a manner designed to drive the phase difference to $90°+\delta\Phi$ and the process is repeated (starting with block 12).

After repeating this process for the fixed number of sense period iterations the final frequency is recorded (block 24). Next, the process is repeated for $-\delta\Phi$, and the frequency corresponding to $-\delta\Phi$ is recorded (block 24). Absent temperature shift during sensing, the phase lock frequency for phase shift $\delta\Phi$ minus the phase lock frequency for phase shift $-\delta\Phi$, yields damping. To correct the final reading for possible temperature drift, however, the process is run again for $+\delta\Phi$ with the two resultant final frequencies for $+\delta\Phi$ being averaged. Finally, damping is computed from the difference between the averaged frequency value for +δΦ and the frequency value for −δΦ (block 28). In the case where fluid viscosity is being measured, viscosity is computed from the measured damping value.

Figure 2:
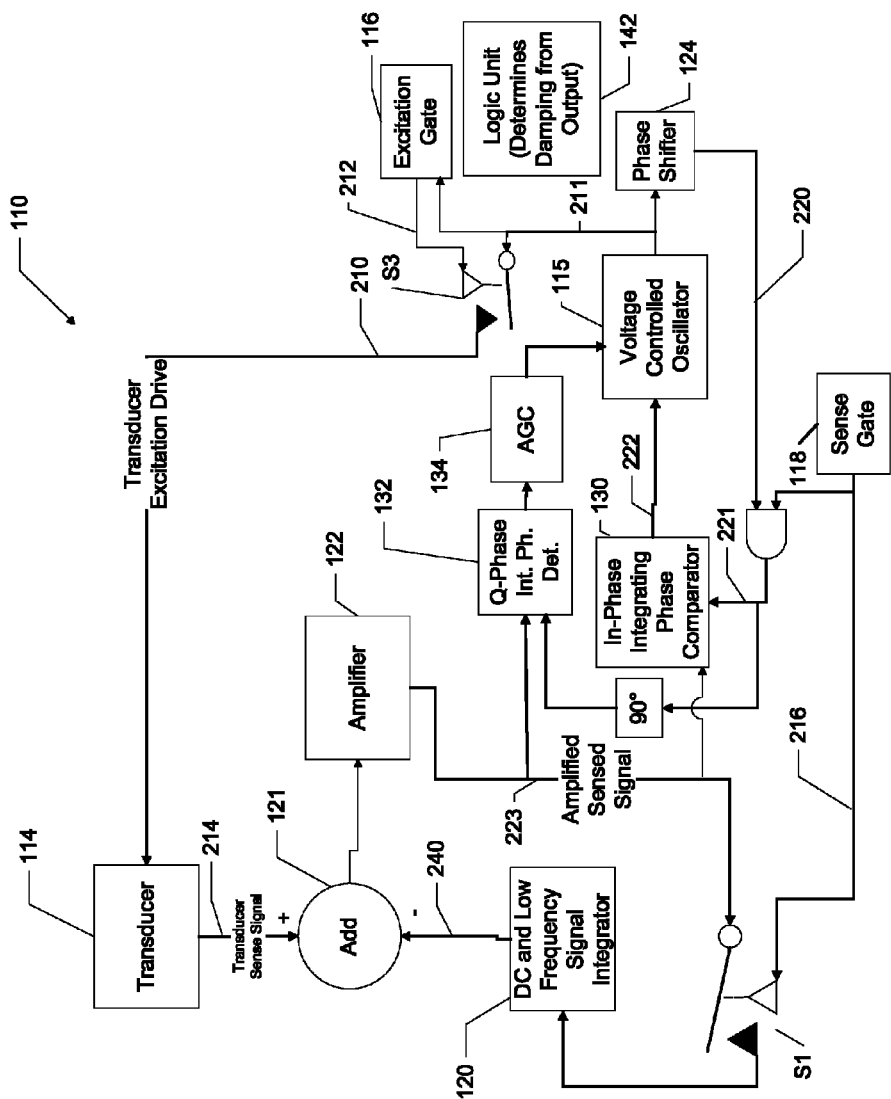
FIG. 2 is a functional block diagram of a preferred embodiment of the present invention in the form of a viscosity measuring device.
Figure 3:
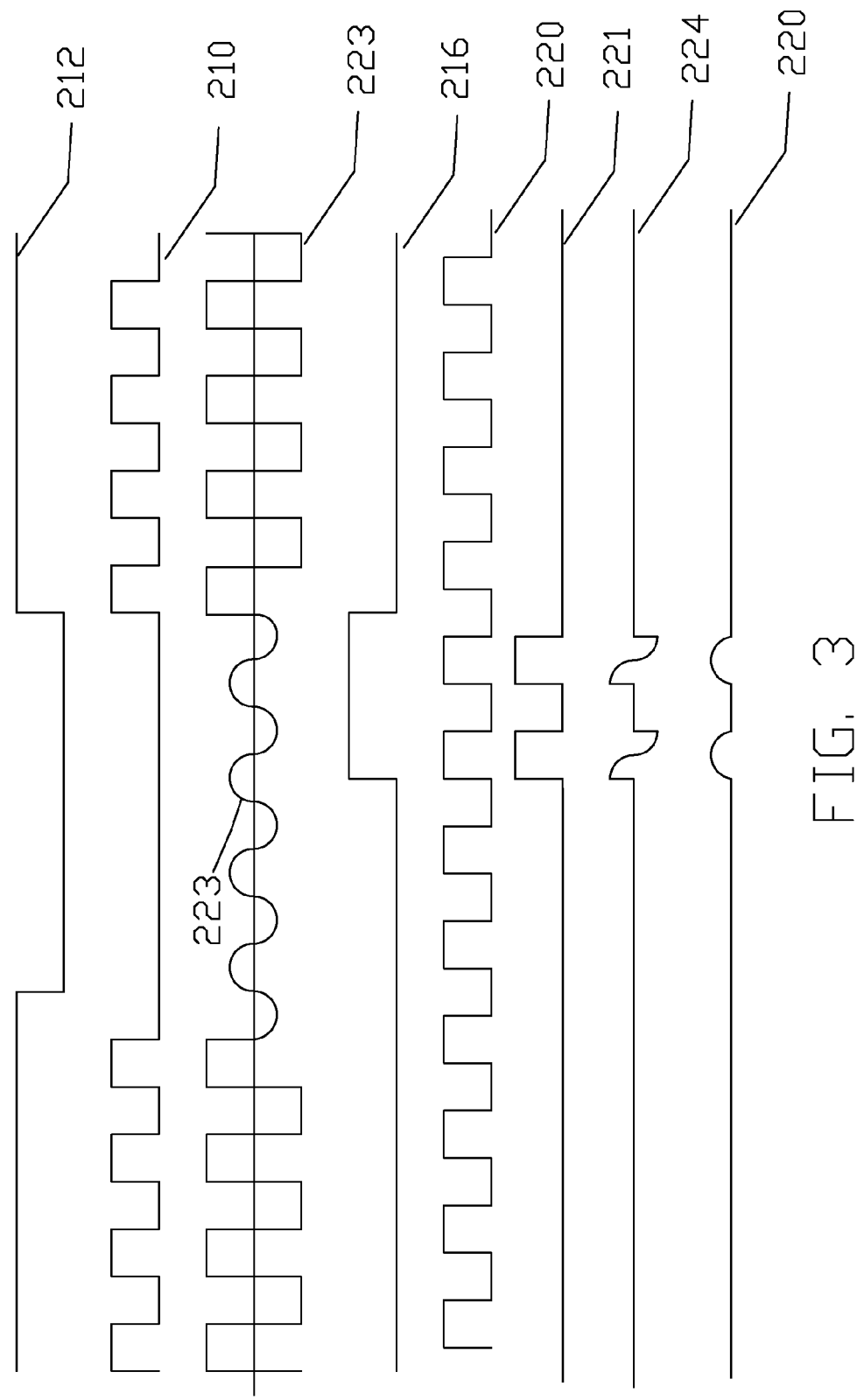
FIG. 3 is an illustration of the waveforms used in the device of FIG. 2.

Referring to FIGS. 1, 2 and 3, in one preferred embodiment the present invention takes the form of a viscometer system 110 in the form of a phase lock loop receiver. System 110 uses a sensor (two configurations of which are shown in FIGS. 12A-12B and 13A-13B and described in the accompanying text), composed of a resonator and a transducer 114. Transducer 114 is used to vibrate (excite, block 12) a resonator and, after a pause (block 14), sense (block 16) the residual vibration. The transducer 114 is driven by excitation signal 210 (FIGS. 2 and 3), which is the output 211 (FIG. 2) of a voltage controlled oscillator (VCO) 115 which is switched on and off by switch S3 controlled by an excitation gate signal 212 (FIG. 3), produced by an excitation gate generator 116.

The sensed signal 214, minus the output 240 of the DC and low frequency signal integrator 120 (described below) drives an amplifier 122, to produce an amplified sensed signal 223 (location shown in FIG. 2). In alternation with the excitation gate signal 212, after a time gap to permit transients produced by the excitation to attenuate, a sense gate signal 216, produced by a sense gate generator 118, changes state causing the phase of the amplified sensed signal 223 to be processed in order to supply a frequency correction signal (block 18). This measurement is performed by an in-phase integrating synchronous detector 130, which determines the phase shift of signal 223 relative to the phase of a phase-shifted signal 220, produced by applying a phase shifter 124 to the VCO output 211. Phase-shifted signal 220 is gated by the sense gate signal 216 to create a reference signal 221. A quadrature integrating synchronous detector 132 performs the same task for the quadrature portion of the signal, which is used to drive the automatic gain control (AGC) 134.

The in-phase detector 130 produces a frequency control signal 222 that is proportional to the integrated measurement of the phase difference of the amplified sensed signal 223 and the phase shifted reference signal 220, which produces a zero result when signals 223 and 222 are 90° out of phase. This frequency control signal 222 in turn drives the VCO 115, so that the excitation frequency produced by the VCO 115, and applied during the next excitation gate will remain unchanged only when the phase difference between signals 223 and 220 is 90°, resulting in no change to the integrated phase difference value. The quadrature detector 132 drives the Automatic Gain Control mechanism 134, which adjusts the signal strength of the voltage controlled oscillator, to maintain the signal strength in the dynamic range of the system 112.

After it settles, the final frequency that results in the specified phase shift δΦ is recorded. As noted previously, in a preferred embodiment the process is permitted to run through a −δΦ iteration and an additional +δΦ iteration, the two frequencies for the +δΦ iterations are averaged together to correct for the effect of possible temperature variation, and the frequency for the −δΦ iteration subtracted from this average, to yield a quantity related to damping, from which a logic unit 142 calculates damping (block 28). The measurement of damping, in turn, yields a measurement of fluid viscosity.

In the innovation of the present invention, a DC and low frequency signal integrator 120 is introduced into the circuit. Integrator 120 is driven by the output of the amplifier 122 during the sense gate signal 216, when a switch S1 is closed. When S1 is open the input voltage to integrator 120 is held constant by a capacitor within unit 120. The integrator 120 output is subtracted from the input of the amplifier 122, by adder 121. Because low frequency signals change slowly relative to the response time of the amplifier 122, all low frequency signals from the transducer are driven to zero at the input (and therefore the output) of amplifier 122. Any DC signal produced by amplifier 122, itself, results in a DC signal of opposite polarity and correct amplitude to negate the DC signal that would otherwise appear at the output of amplifier 122.

Figure 4:
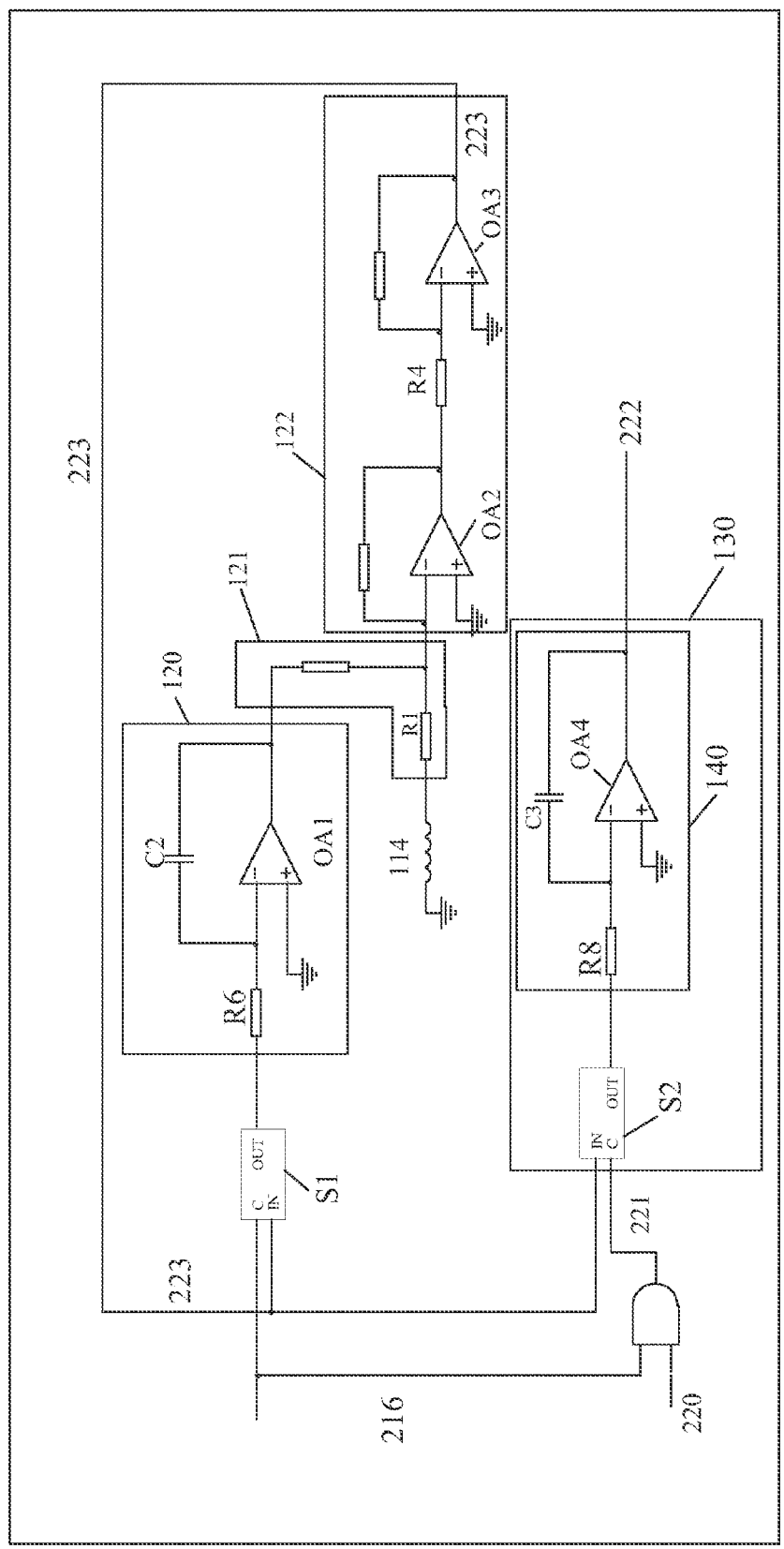
FIG. 4 is a schematic diagram of the receive signal processing portion of the device of FIG. 2.

Referring to FIG. 4, which shows one embodiment of the in-phase signal processing portion of the viscometer 110 in greater schematic detail, integrator 120 is made up of an operational amplifier OA1, an integrating capacitor C1 and resistor R6. The amplifier 122 is made up of a first operational amplifier OA2 driving a second operational amplifier OA3, with resistors R1, R2, R4 and R5 determining the amplification. Resistors R1 and R7 serve as adder 121. In an alternative topology operational amplifier OA2 is included in adder 121.

In-phase detector 130, includes an analog switch S2 that passes the amplified signal 223 when the reference signal 221 is high, to create a demodulated signal 224. An operational amplifier OA4, resister R8 capacitor C3 form an integrator 140 for this signal, and this drives the VCO 115. When reference signal 221 is exactly 90° out of phase with amplified sensed signal 223, demodulated signal 224 integrates to zero. This is because under this condition signal 221 transitions from zero to one at the peak of signal 223 and then transitions from one to zero at the negative peak of signal 223, so that a perfect half-cycle of signal 223, with the negative quarter-cycle canceling the positive quarter-cycle, is sent to the integrator 140. When this relationship occurs, the output of the demod integrator 140 will not change from one iteration to the next, and the system 110 will be in phase-lock state.

Returning to the integrator 120, skilled persons will recognize that the time constant, and therefore the frequency response, of integrator 120 is set by the values of the capacitor and resistor, C1 and R6, respectively. The value of $1/(2\pi*R6*C1)$ sets the 3 db point of the circuit, at which an input signal is attenuated by a factor of 0.5 from its input value. Accordingly, if the product C1*R6 of these two values were set equal to 0.02, for example, the 3 db frequency would be approximately 8 Hz. This is a realistic value for this type of circuit because many physical vibrations representing ambient noise would be in the 1 Hz range. A value of 100K for the resistor and of 0.2 μF for the capacitor would yield this value, and represent reasonable values for the circuit. Clearly, however, the value can be set over a range and depending on the application, it may be desirable to set the 3 dB attenuation point to anywhere from 5 Hz to 10,000 Hz. In one preferred embodiment the 3 dB point is set at about 100 Hz to reject ambient noise caused by rotating machinery. Other values outside of this range may be warranted for some applications.

Figure 5:
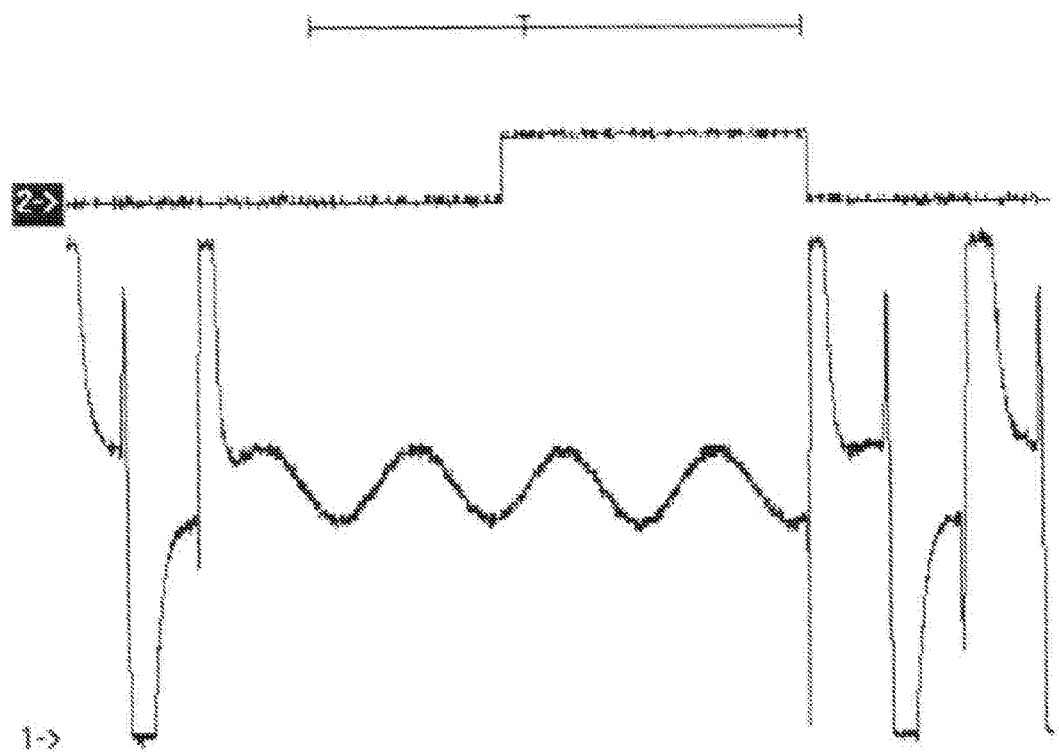
FIG. 5 is a graph of the amplified sensed signal response of a system according to the present invention to an oscillating input signal.
Figure 6:
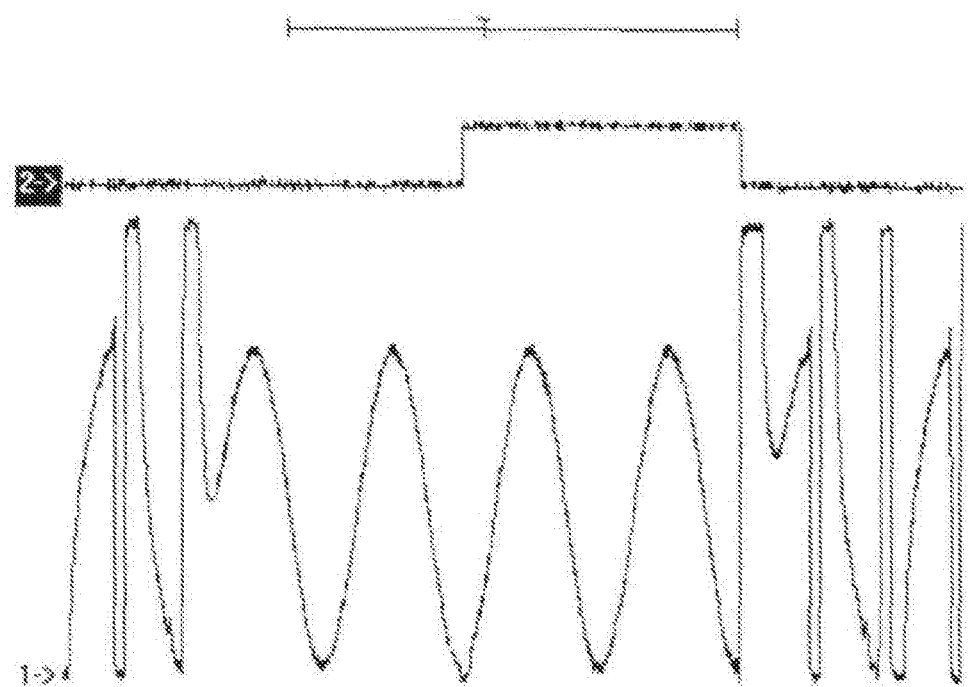
FIG. 6 is a graph of the prior art system that does not include the DC offset and low frequency integrator of the system of FIG. 5, with a DC offset added to cancel the DC signal produced by the system, but where this added DC offset is deliberately set too small to fully cancel this DC signal.
Figure 7:
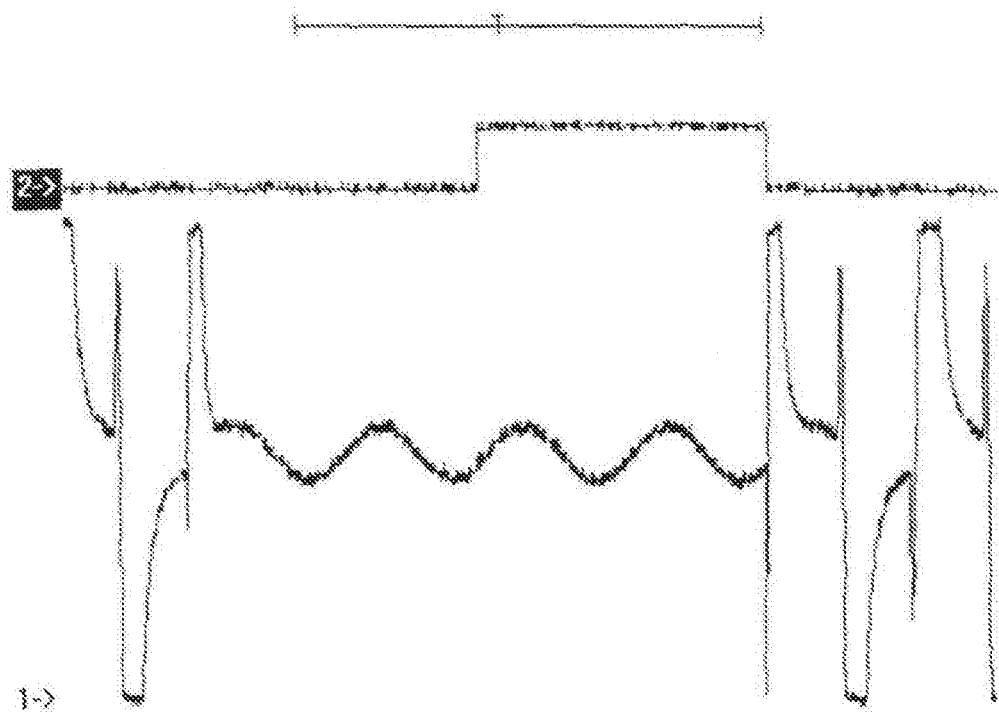
FIG. 7 is a graph of the response of the system of FIG. 6, with a DC offset added to the signal to cancel the DC offset produced by the signal amplifier, but where this added signal is deliberately slightly too large.

FIGS. 5-11 are graphs that collectively show system performance improvements obtained by the introduction of integrator 120. FIGS. 5-7 taken together illustrate the effect of partially uncompensated DC offset. FIG. 5 shows an oscilloscope trace of the received amplified signal 223 during normal operation of system 110. For experimental purposes, however, a prior art system identical to that of system 110, except for the absence of integrator 120 is used and a DC signal is introduced into the inverting input of operational amplifier OA2 (using the same reference numbers for the prior art system). This signal is connected to the inverting input of OA2 through a 52 kΩ resistor and is calibrated by being hand adjusted until the amplified signal 223 appears as it does in FIG. 5, yielding an offset compensation value of 2.497 volts. To determine the effect of not fully compensating for the DC offset, the introduced DC signal is adjusted so that it is 14 mvolts lower than the 2.497 volt compensation value, yielding the graph of FIG. 6, in which amplified signal 223 is pulled negative during the sense gate. Also, because of the partially uncompensated DC offset the automatic gain control (AGC) is misdirected, causing an increase in signal amplitude. FIG. 7 shows the response of signal 223 to an injected voltage that is higher than the compensation voltage by 3 mvolts, driving the signal up and misdirecting the AGC in the opposite manner to that of the FIG. 6 case, thereby reducing the signal amplitude. When the conditions of FIGS. 6 and 7 are repeated for system 110, the resultant amplified signal looks essentially identical to that of FIG. 5, as the integrator 120 completely compensates for the injected signal. In fact, even when the injected voltage differs from the offset compensation value by 2 volts, there is no discernable effect on the trace of signal 223.

Figure 8:
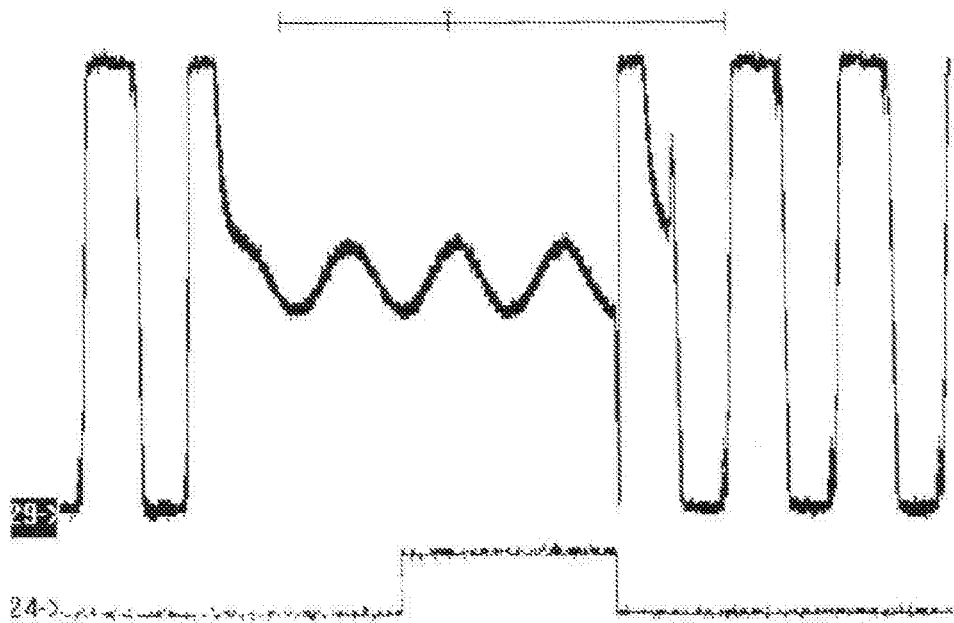
FIG. 8 is a graph showing 5 traces, each showing a response of the system of FIG. 6 to a signal that includes 120 Hz noise at 100 mV.
Figure 9:
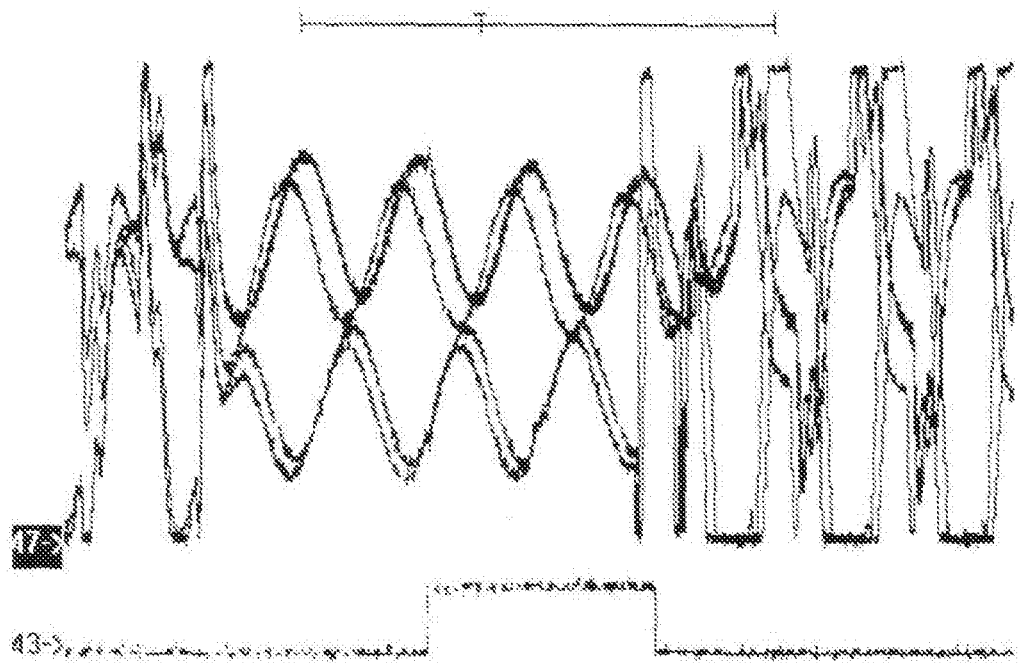
FIG. 9 is a graph showing 5 traces, each showing a response of the system of FIG. 6 to a signal that includes 120 Hz noise at 2 Volts.
Figure 10:
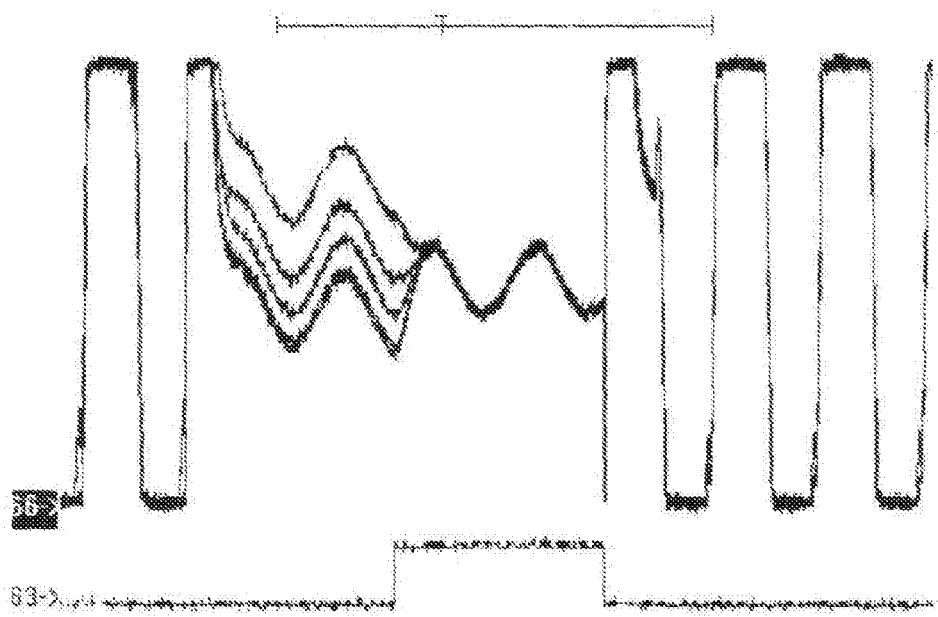
FIG. 10 is a graph showing 5 traces, each showing a response of the system of FIG. 5 to the same signal that produced the traces of FIG. 9.
Figure 11:
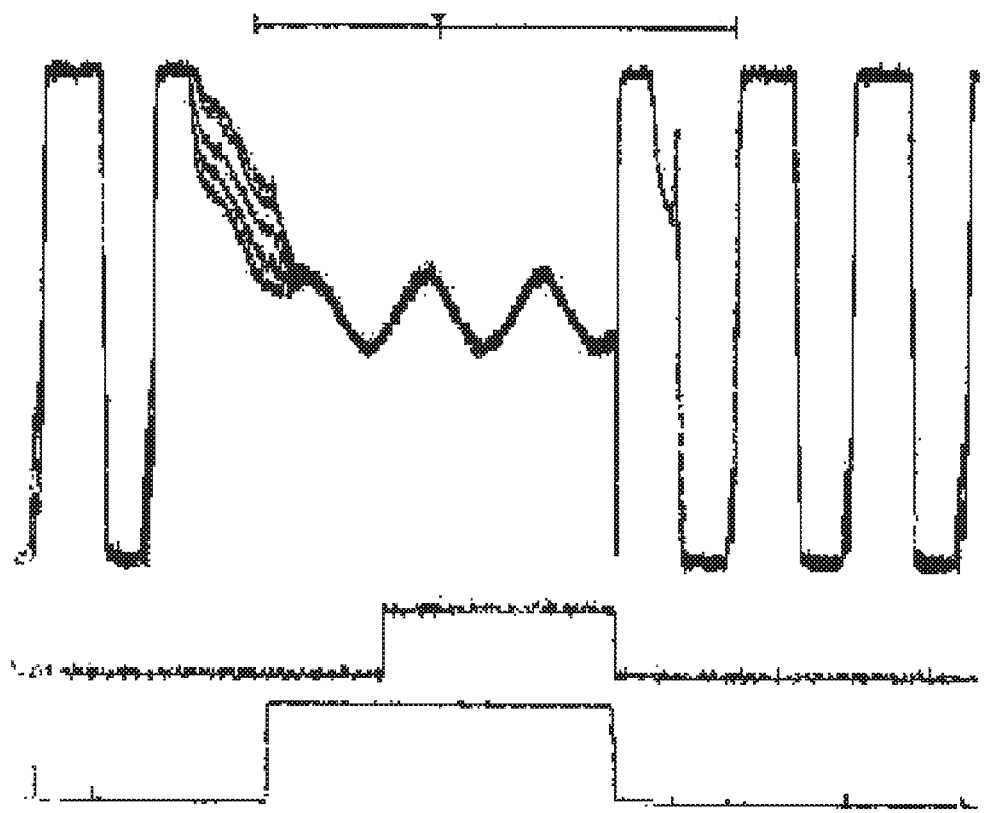
FIG. 11 is a graph showing 5 traces, each showing a response of the system of FIG. 5, to the same signal that produced the traces of FIG. 10, except for that the DC and Low Frequency Integrator is activated a period earlier than in FIG. 10.

FIGS. 8-11 illustrate the effect of different integrator 120 time constants in filtering out 120 Hz input noise of varying amplitudes. FIG. 8, shows the amplified signal 223 of system 112, when the time constant τ for the integrator 114 is $5\times10^{-2}$ and 100 mvolts, 120 Hz noise has been injected through a 1 MΩ resistor to the non-inverting input of operational amplifier OA2 (FIG. 4). In FIG. 8 and the following graphs the input frequency equals the resonator third harmonic (@19,444 Hz), which will be discussed in greater detail below. Five superimposed traces are shown. Although the added noise is evident in the greater variation of the traces, no significant detriment is caused. FIG. 9, shows the response of a system identical to that of FIG. 8, but where the 120 Hz input noise has an amplitude of 2 volts, simulating noise that might be introduced into a fluid being measured by, for example, a pump. Five separate traces are shown superimposed. In this case the time constant of integrator 120 is not low enough to prevent the system response from being severely degraded by the noise, so that although phase lock is maintained, signal 223 is not at all consistent from one trace to the next, causing large errors in the measured damping. When the amplitude of the input noise is raised to 3 volts, phase lock is lost and the system ceases to function. FIG. 10 shows the system response to the exact same signal input conditions, but this time with the integrator time constant decreased to $5\times10^{-4}$. By reducing the value of capacitance by a factor of 100 the range of frequency addressed by the integrator is increased by the same factor. As can be seen, the response during the time the integrator 120 is active quickly becomes uniform between iterations. FIG. 11 shows the same system and waveform input as FIG. 10, but in this case the integrator is switched on a period before the sense gate begins, during the dead time between excitation and sensing. By the time the sense gate switches on, the waveform is completely stabilized, eliminating the error due to the simulated vibrational disturbance.

Figure 12C:
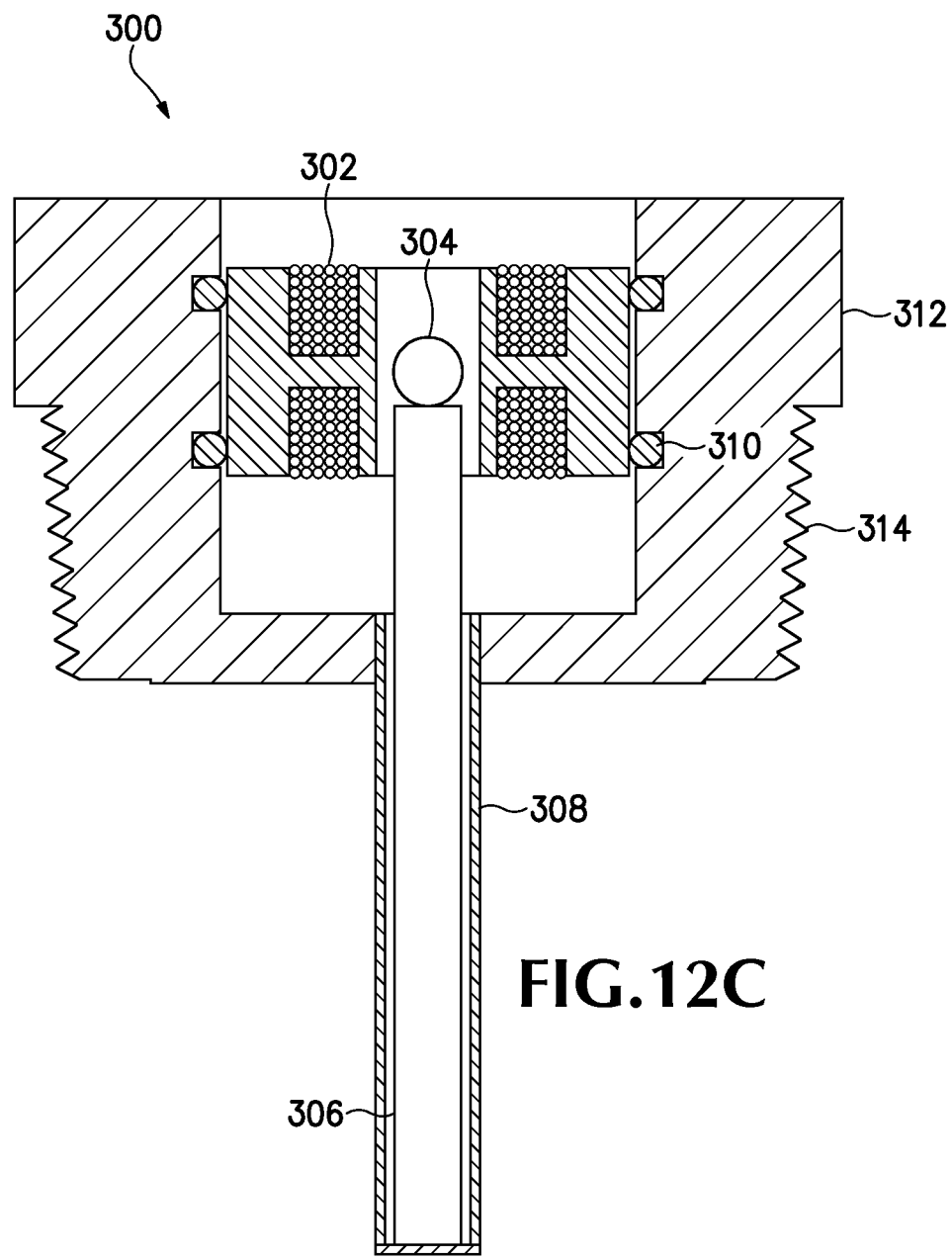
FIG. 12C is a cross-sectional view of the transducer configuration of FIG. 12A, taken along view line C-C.

FIGS. 12A-12C show a cross-sectional view of viscometer transducer 114. A coil 302 is used to apply magnetic force to a resonator 303, made up of a resonator permanent magnet (304), inner tube 306, and outer tube 308, which is attached to inner tube 306 at the end furthest from magnet 304. The resonator permanent magnet 304 is driven by the electromagnet flux created by coil 302 and in turn physically drives inner tube 306, which physically drives outer tube 308. The direction of the current through coil 302 alternates at the fundamental frequency, causing the resonator 303 to move rotationally back and forth at the fundamental frequency. The viscosity of the fluid being measured damps the motion of the outer tube 308. It is this damping that is measured by system 110, in order to form a measurement of viscosity. The coil 302 is held in place within a sensor body 312 and vibrationally isolated from body 312 by O-rings 310. Sensor body 312 includes threads 314 to facilitate the placement of transducer 114 in the side of a pipe or tank.

Figure 13:
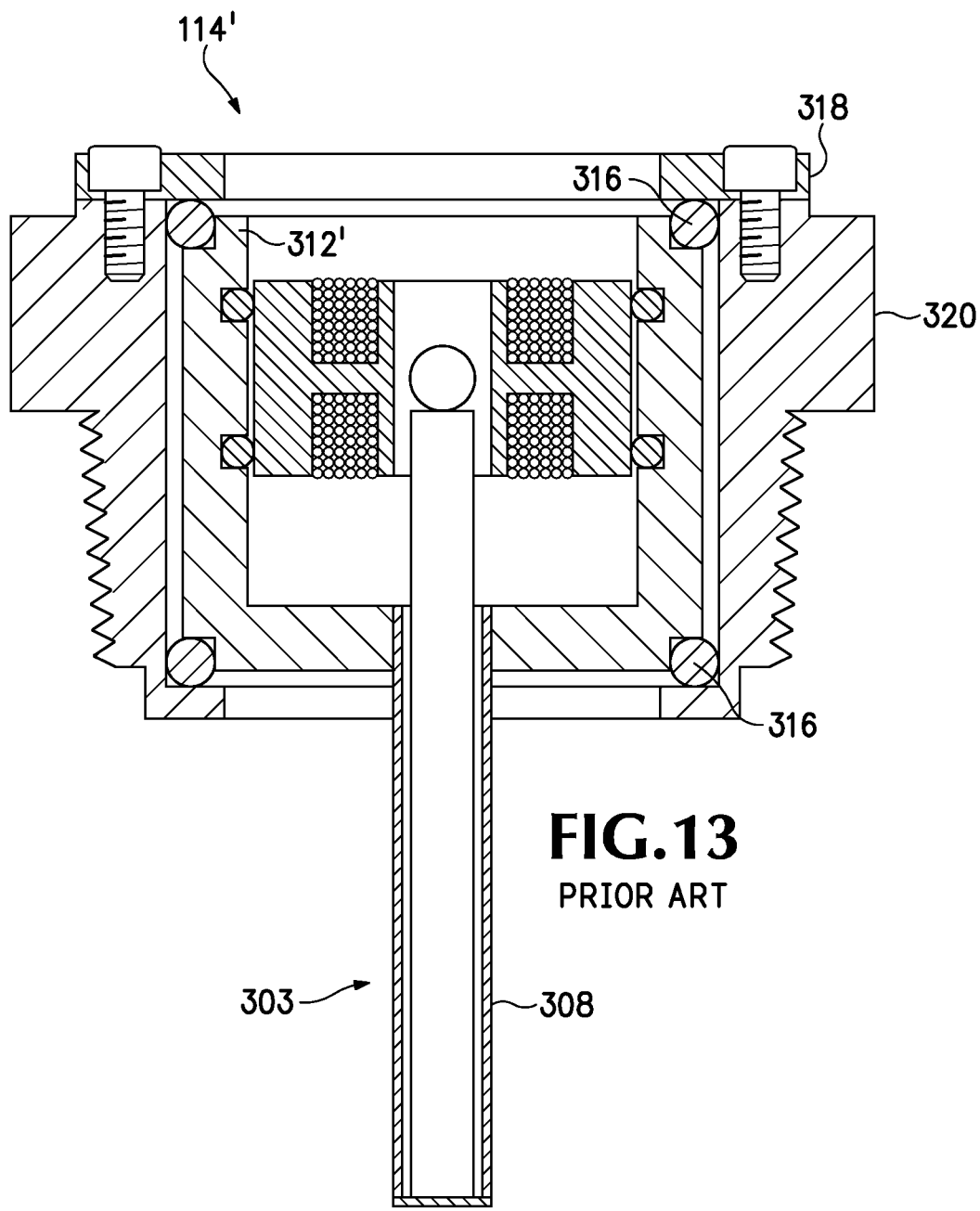
FIG. 13 is a cross-sectional view of a transducer configuration from the prior art, but which could be used in the system of the present invention.

Referring to FIG. 13, in a prior art transducer configuration 114', sensor body 312' is held in place in an outer housing 320 by a pair of rubber sensor-mounting O-rings 316, one of which is held in place by a sensor retaining ring 318. O-rings 316 are necessitated by the need to run prior art viscometers at the resonator fundamental frequency. As explained further below, the improvements to signal processing yielded by the system 110 make practical transducer 114, which does not include sensor mounting O-rings 316. The elimination of the rubber O-rings 316 makes transducer 300 more compact, easier to clean, less vulnerable to chemical and thermal attack and more robustly sealed. Accordingly, the newly practical transducer 300 expands the applications of viscometers.

The O-rings 316 act to isolate outer housing 320 from the vibrations of outer resonator tube 308, which could otherwise cause parasitic resonances in a structure to which transducer 114' was attached, when resonator 303 is run at its fundamental frequency. A system in which parasitic resonances may distort the measurement is unreliable and therefore impractical. But the possibility that low frequency noise would cause the phase-lock loop system to break phase lock prevented the use of higher resonator vibrational modes in prior art systems.

Because the DC and low frequency integrator 120 prevents low frequency noise from causing the system to break lock on a higher frequency, driving the resonator at its second torsional mode (whose frequency is typically 3 times that of its fundamental mode), becomes practical in system 110. The second torsional mode, however, causes the outer tube vibration to apply less force to transducer body 312, by dividing the vibration into three zones, each of which has a lower amplitude and applies less force to its zone endpoints than vibration in a single zone, at the fundamental frequency. Accordingly, the possibility of parasitic resonances is greatly reduced.

Figure 14A:
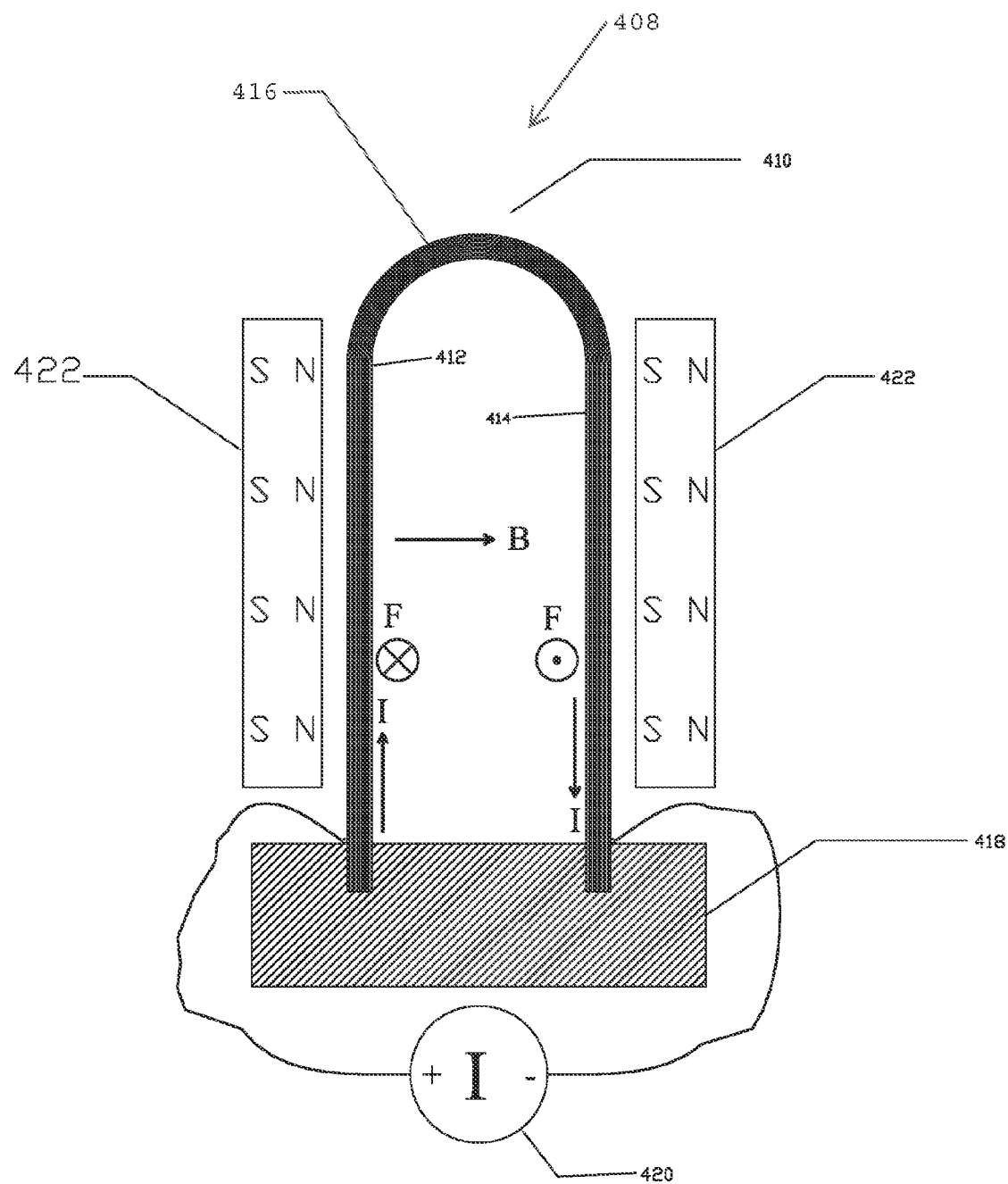
FIG. 14A is an illustration of an additional alternative preferred embodiment of a transducer configuration.

Referring to FIG. 14A, in an additional preferred embodiment the function of transducer 114 is performed by specific transducer configuration 408, which includes an elastic conductive hairpin loop 410. A measurement of the damping of induced vibrations in this loop 410, as performed by system 110, can be used to determine the properties of a fluid in which the loop has been introduced. These properties are not limited to fluid viscosity, but include density and elasticity. In addition, a system 110, equipped with transducer 408 can be used to measure the damping and elasticity of gels and other mechanically compliant solids In one preferred embodiment, the loop 410 is made of an elastic wire, made of a metal, such as copper, stainless steel or silver. In alternative preferred embodiment, however, similarly loop-shaped conductors are composed of other materials fabricated in forms other than wire, for example, from etched, selectively conductive silicon, or from insulators such as ceramics or glass made conductive by metallization or other processes.

The loop 410, all of which is conductive and elastic, includes a first leg 412, a second leg 414 and a bridge 416 joining the two. Also, a massive, electrically insulating base 418 supports loop 410. A current source 420, drives a current through the loop 410. Additionally, a pair of magnets 422 create a magnetic field that is traversed by loop 410. Accordingly as current is passed through loop 410, it is pushed by a mechanical force proportional at each point to the vector product of the magnetic field and the current through that segment, causing a mechanical distortion of loop 410. As the current direction in legs 412 and 414 is mutually opposed, this creates opposite forces in legs 412 and 414, acting to twist loop 410, as shown in FIGS. 14B, 14C and 14D. Furthermore, because the material of the loop 410 possesses both inertia due to its mass, and elasticity, when the loop 410 is distorted and released, it will vibrate at one of its characteristic frequencies, thereby having a set of vibratory modes. If the current source produces an alternating current, its frequency may be adjusted such as to preferentially excite one of the resonant modes of the wire loop.

Figure 15A:
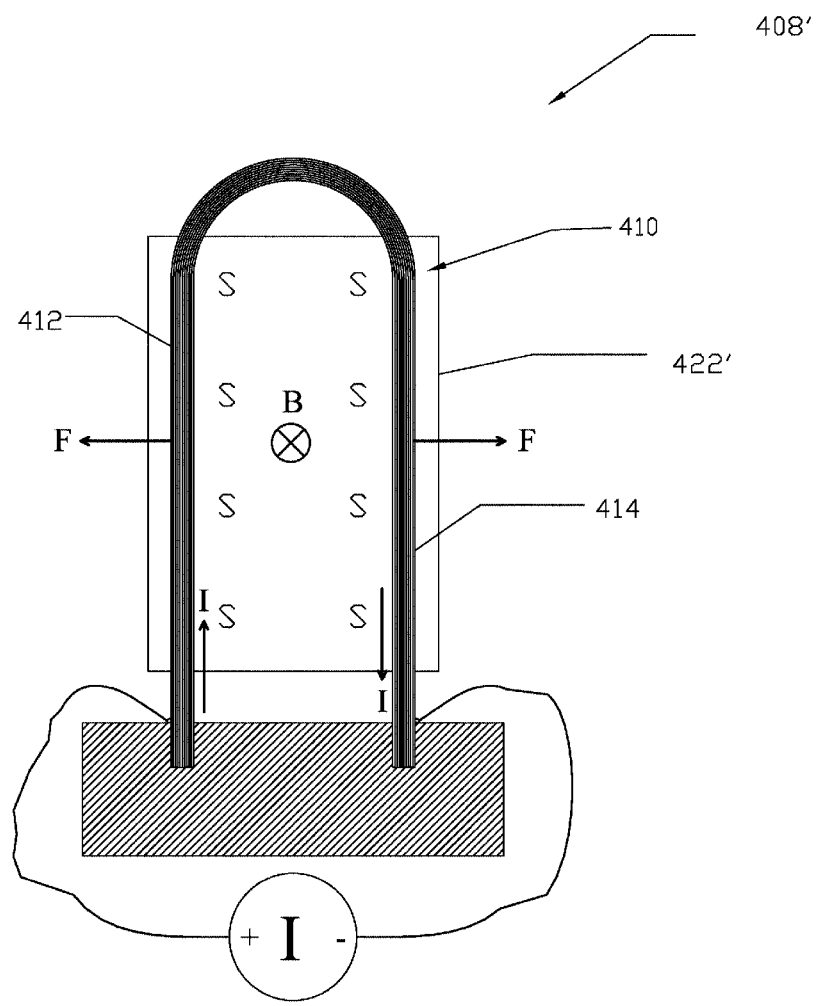
FIG. 15A is an illustration of another additional alternative preferred embodiment of a transducer configuration.
Figure 15B:
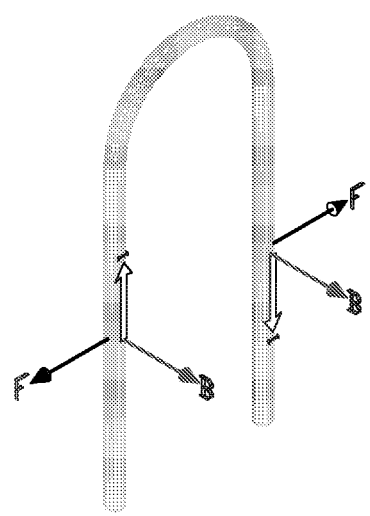
FIG. 15B is an additional illustration of the transducer configuration of FIG. 15A, showing the direction of magnetic flux.
Figure 15C:
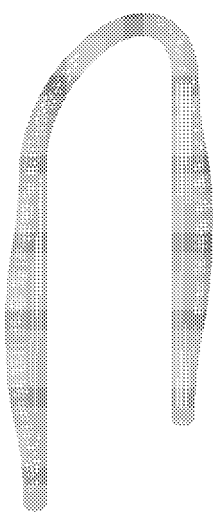
FIG. 15C is another additional illustration of the transducer configuration of FIG. 15A, showing planar distension of the wire loop.
Figure 15D:
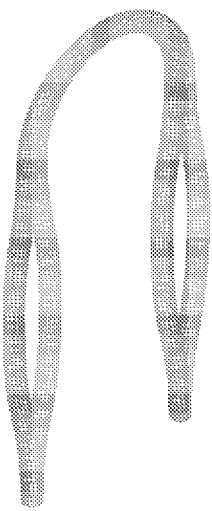
FIG. 15D is still another additional illustration of the transducer configuration of FIG. 15A, showing maximum planar distension of the wire loop.

Referring to FIG. 15A, a transducer configuration 408' includes magnets 422' that are positioned behind and in front (not shown) of the loop 410, with opposing poles facing each other. The resulting magnetic field is perpendicular to the plane of the loop 410, so that the force on the legs 412 and 414 of the loop is in the plane of the loop 410, and either inward toward its symmetry axis, or outward away from its symmetry axis depending on the polarity of the current source 420. The legs of the loop function like the tines of a tuning fork in which the tips of the tines are connected by an elastic member. This is shown in FIGS. 15B, 15C and 15D. FIG. 15B illustrates the magnetic, current and force vectors (which, as will be familiar to skilled persons, are designated in FIGS. 15A through 16D by standard designators "B", "I", and "F", respectively) operating on the loop 410. FIG. 15C shows the static distortion of the loop 410 compared to its initial undistorted shape. FIG. 15D shows the limits of the motion of the loop 410 when it is driven by magnets 422' as shown in FIG. 15A.

Figure 16A:
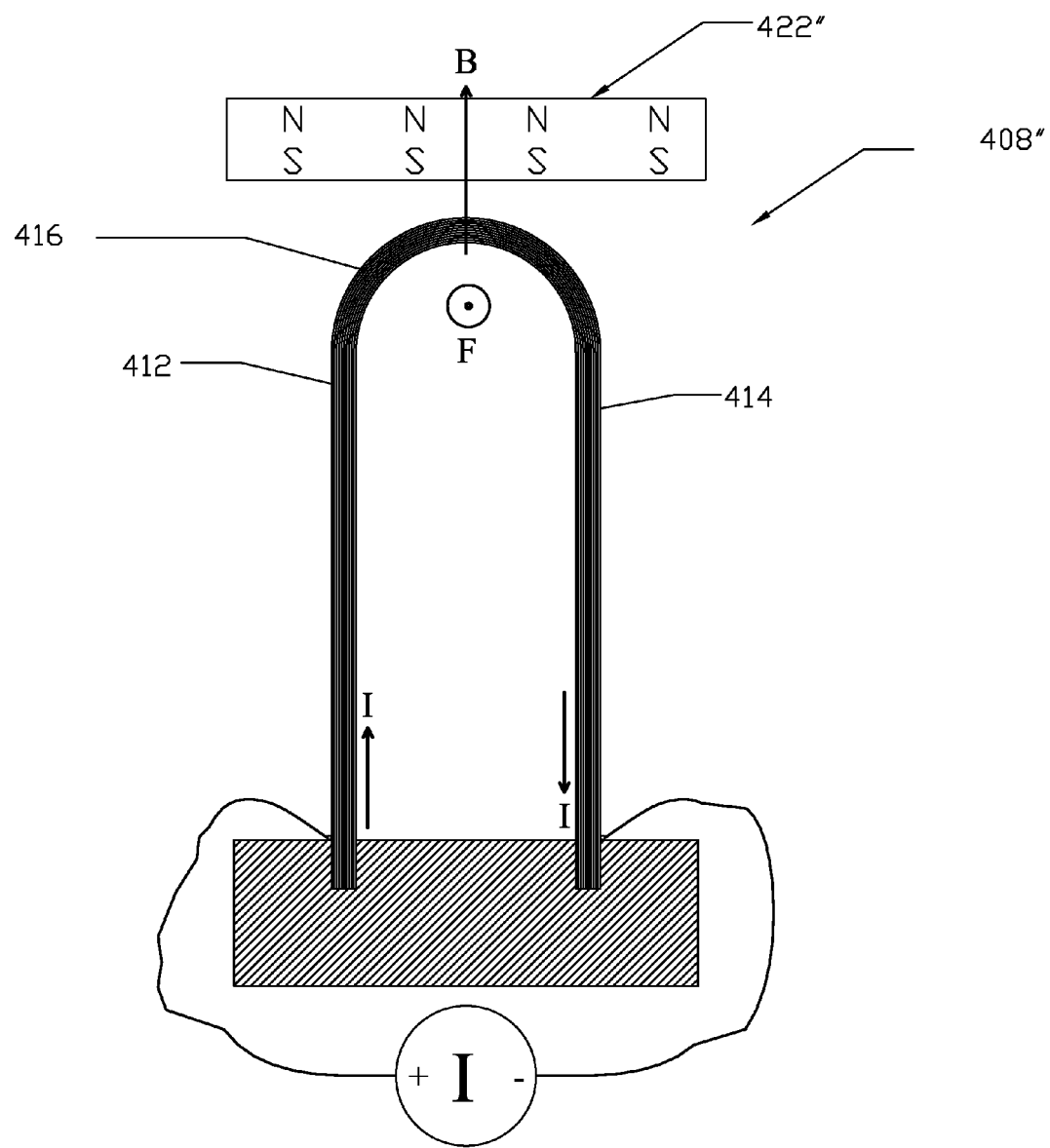
FIG. 16A is an illustration of another additional alternative preferred embodiment of a transducer configuration.
Figures 16B, 16C, 16D:
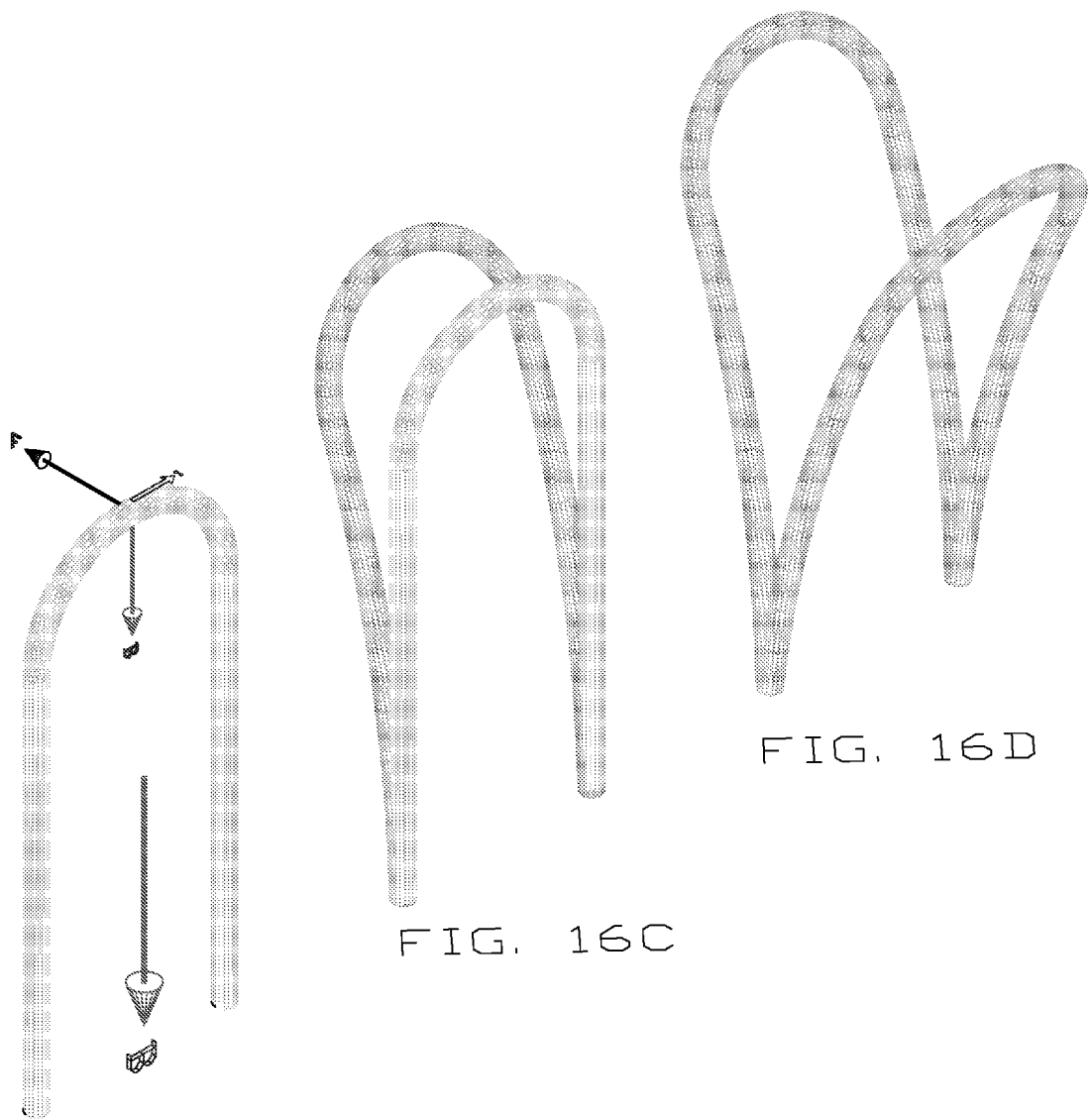
FIG. 16B is an additional illustration of the transducer configuration of FIG. 16A, showing the direction of magnetic flux.
FIG. 16C is another additional illustration of the transducer configuration of FIG. 16A, showing bending of the plane of the wire loop.
FIG. 16D is still another additional illustration of the transducer configuration of FIG. 16A, showing maximum bending of the plane of the wire loop.

Referring FIG. 16A, a transducer configuration 408" includes a magnet 422" that is positioned above the arch 416 of the loop 410. Referring to FIG. 16B, the magnetic field of magnet 422 is parallel to the plane of the loop and parallel to the current flow in its legs 412 and 414, with only bridge 416, which is not parallel to the field, experiencing a force, resulting in bridge 416 being pushed into and out of the paper, as shown in FIG. 16C and with FIG. 16D showing the limits of the motion of the loop when driven in the transducer configuration 408".

When the loop is immersed in a fluid or compliant solid, each of the transducer configurations 408, 408' and 408" produces a somewhat different pattern of flow or distortion in the medium. The vibrational characteristics created by the differing transducer configurations 408, 408' and 408" will be influenced to differing degrees by the characteristics of the medium. Therefore, the transducer configuration, and therefore the vibratory frequencies, can be selected to separate the effects of various properties of the medium. Moreover, in additional preferred embodiments the magnets are not oriented the along a principal axis of the loop, as is shown in FIGS. 14A, 15A and 16A. In one preferred embodiment of a transducer configuration, the magnetic field is oriented at a nonzero angle to each of the principle axes, permitting all of the mode geometries cited above to be generated by a single transducer configuration.

Skilled persons will recognize that the embodiments of FIGS. 14A-16C may be utilized in the manner described with reference to FIGS. 1-4, by periodically halting the excitation current, during the time that the excitation current is off, measuring the current through the loop 410 and then processing this sensed current to determine the physical characteristics of the medium being tested. Skilled persons will also recognize that many other permutations of wire-based fluid parameter measurement devices are possible. For example, a straight wire could be used and would be subject to force when current flowed through it, similar to a leg of one of the above-described embodiments. Another example of the many possible geometries, would be a wire that includes a sharp bend at its distal end, which could be used to broach a membrane covering a fluid. Also, lithographic manufacturing techniques could be used to create a loop having a precisely defined geometry.

Many variant embodiments also exist for the arrangement of the magnets. For example, although two magnets are shown in the embodiments of FIGS. 14A and 15A, a single magnet could suffice to create the required magnetic field, for the wire geometries shown. Alternatively, a magnetic loop could be used to create the required magnetic field.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of measuring properties of a medium that is a fluid or compliant solid, such as a gel, comprising:
    (a) providing a conductor electrically connected to a current source, so as to permit said current source to send a current through said conductor;
    (b) creating a magnetic field about said conductor;
    (c) introducing said conductor into said medium;
    (d) periodically sending a current waveform, having a frequency, through said conductor, so as to cause said conductor to move, due to force exerted on said conductor from interaction of said current and said magnetic field;
    (e) alternately sensing the conductor current and producing a sense signal at a sense signal node;
    (f) amplifying said sense signal to produce an amplified sense signal;
    (g) measuring the phase relationship between said current waveform and said amplified sense signal;
    (h) adjusting said current waveform frequency so as to create a phase lock loop;
    (i) measuring said frequency when said phase lock loop is in lock state and calculating fluid properties from said measured frequencies.

2. The method of claim 1, wherein said conductor is an elastic wire.

3. The method of claim 2, wherein said elastic wire is a bare, un-insulated wire.

4. The method of claim 1, wherein said conductor is composed of etched, selectively conductive silicon.

5. The method of claim 1, wherein said conductor is composed of metallization on a substrate.

6. An apparatus for measuring properties of a fluid or compliant solid, such as a gel, comprising:
    (a) a conductor electrically connected to a current source, so as to permit said current source to send a current through said conductor;
    (b) a magnet placed to create a magnetic field about said conductor;
    (c) a controller connected to said current source and commanding said current source to periodically send a current waveform, having a frequency, through said conductor, so as to cause said conductor to move, due to force exerted on said conductor from interaction of said current and said magnetic field;
    (d) a current sensor adapted to sense the conductor movement by sensing electrical current through said conductor during periods when said current source is not sending said current waveform through said conductor and thereby producing a sense signal at a sense signal node;

(e) an amplifier responsive to said sensor to amplify said sense signal to produce an amplified sense signal;

(f) a phase detector adapted to measure phase relationship between said current waveform and said amplified sense signal;

(g) wherein said current source controller is responsive to said phase detector and is adapted to cause said current source to adjust said current waveform frequency so as to create a phase lock loop;

(h) a frequency detector to detect said current waveform frequency when said phase lock loop is in lock state;

(i) a logic unit to calculate fluid properties from said measured frequency.

7. The apparatus of claim 6, wherein said conductor is an elastic wire.

8. The apparatus of claim 7, wherein said wire forms a sharp point, which can be used as a broaching tool.

9. The apparatus of claim 6, wherein said conductor is U-shaped, and defines a plane.

10. The apparatus of claim 9, wherein said magnet faces said plane.

11. The apparatus of claim 9, wherein said U-shape of said conductor includes legs joined by an arch and said magnet is intersected by said plane and has a face that is parallel to said legs.

12. The apparatus of claim 9, wherein said U-shape of said conductor includes legs joined by an arch and said magnet is intersected by said plane and has a face that is perpendicular to said legs.

13. The apparatus of claim 6, wherein said conductor is a bare, un-insulated elastic metal wire.

* * * * *